United States Patent
Bronshtein (10) Patent No.: US 11,260,024 B2
(45) Date of Patent: Mar. 1, 2022

(54) POLYMERIC COMPOSITIONS CONTAINING AMBIENT-TEMPERATURE STABLE BIOPHARMACEUTICALS AND METHODS FOR FORMULATION THEREOF

(71) Applicant: UNIVERSAL STABILIZATION TECHNOLOGIES, INC, San Diego, CA (US)

(72) Inventor: Victor Bronshtein, San Diego, CA (US)

(73) Assignee: UNIVERSAL STABILIZATION TECHNOLOGIES, INC, San Diego, CA (US)

(*) Notice: Subject to any disclaimer, the term of this patent is extended or adjusted under 35 U.S.C. 154(b) by 0 days.

(21) Appl. No.: 16/368,757

(22) Filed: Mar. 28, 2019

(65) Prior Publication Data

US 2019/0240147 A1    Aug. 8, 2019

Related U.S. Application Data

(63) Continuation of application No. 14/292,809, filed on May 30, 2014, now Pat. No. 10,272,033.

(60) Provisional application No. 61/956,079, filed on May 31, 2013.

(51) Int. Cl.
*A61K 9/00* (2006.01)
*A61K 35/741* (2015.01)

(52) U.S. Cl.
CPC .......... *A61K 9/0021* (2013.01); *A61K 35/741* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2008/0229609 A1* | 9/2008 | Bronshtein | A01N 1/0284 34/287 |
| 2009/0148518 A1* | 6/2009 | Brown | A61K 9/4816 424/457 |
| 2010/0172993 A1* | 7/2010 | Singh | A61K 9/19 514/1.1 |
| 2011/0195124 A1* | 8/2011 | Jin | A61K 9/0021 424/486 |

* cited by examiner

*Primary Examiner* — David J Blanchard
*Assistant Examiner* — Sarah J Chickos
(74) *Attorney, Agent, or Firm* — CP Law Group PC; Cy Bates (57) ABSTRACT

Biopharmaceuticals, such as vaccine agents and probiotics, are encapsulated in carbohydrate-glass particles and embedded in an amorphous polymer substrate to produce polymeric compositions containing ambient-temperature stable biopharmaceuticals for syringeless administration to patients such as via dissolvable films, micro-needle patches and similar medical delivery devices. The amorphous polymer substrate is soluble in both water and a volatile organic solvent, yet the carbohydrate-glass particles are insoluble in the volatile organic solvent.

16 Claims, 4 Drawing Sheets

FIG.1

```
Freeze Drying  → OR →  Spray Drying  → OR →  Foam Drying
``` obtaining an amount of ambient-temperature stable biopharmaceuticals micronized for delivery dissolving hydroxypropyl cellulose (HPC) and triacetin (glycerin triacetatein) in acetone to form a polymer solution introducing said ambient-temperature stable biopharmaceuticals into said polymer solution evaporating the acetone from said polymer solution containing ambient-temperature stable biopharmaceuticals

*FIG.7*

# POLYMERIC COMPOSITIONS CONTAINING AMBIENT-TEMPERATURE STABLE BIOPHARMACEUTICALS AND METHODS FOR FORMULATION THEREOF

CROSS-REFERENCE TO RELATED APPLICATIONS

This application is a continuation of U.S. Ser. No. 14/292,809, filed May 30, 3014, titled "POLYMERIC COMPOSITIONS CONTAINING AMBIENT-TEMPERATURE STABLE BIOPHARMACEUTICALS & METHODS FOR FORMULATION THEREOF";

which '809 application claims benefit of priority with U.S. Provisional Application Ser. No. 61/956,079, filed May 31, 2013, titled "POLYMERIC FILMS AND PATCHES INCORPORATING THERMOSTABLE BIOTHERAPEUTICAL POWDERS FOR NEEDLE-FREE DELIVERY";

the entire contents of each of which are hereby incorporated by reference.

STATEMENT REGARDING FEDERALLY SPONSORED RESEARCH

This invention was made with government support under R21AI094508 "Thermostable Vaginal Probiotic Microbicide" awarded by the National Institute of Health (NIH). The government has certain rights in the invention.

TECHNICAL FIELD

This invention relates to compositions and delivery devices useful for delivery of biopharmaceuticals to patients, and methods for formulation of such compositions; and more particularly, to such compositions containing ambient-temperature stable biopharmaceuticals for syringeless administration.

BACKGROUND ART

The tremendous reduction in global morbidity and mortality achieved through world-wide immunization programs relies directly upon the capacity to manufacture sufficient vaccines at an affordable price, especially in the developing world, and upon maintaining the vaccine potency up to the time of delivery, even under extreme environmental conditions (Duclos et al. 2009).

Most vaccines are currently stored and distributed in freeze-dried (lyophilized) form. At the point of delivery, lyophilized vaccines must be reconstituted with diluent, typically sterile water, that is shipped with the vaccine. Most of these vaccines are delivered by injection with a syringe and needle. The major drawbacks of this method include needle-stick injuries to health care workers (Panlilio et al. 2004), needle-phobia and discomfort for patients facing increasingly crowded immunization schedules (Miller and Pisani 1999), and the costs and complexity of safe disposal of sharps in the medical waste stream. In the developing world, unsafe injection practices such as reuse of needles represent a risk to patients many times higher than needle-stick injuries to health care workers (Gyawali et al. 2013). An estimated 16 billion injections are given annually in the developing world. Unsafe injections were estimated in 1999 to cause 1.3 million deaths annually and to cost more than $535 million to treat bloodborne diseases transmitted by unsafe injection. It is estimated that unsafe injections infect more than 88,000 people with HIV annually (Hutin et al. 2003).

There are many possible solutions to resolving the global problem of needle-stick injuries and unsafe injections, including reducing unnecessary injections, improving injection practices, improving sharps waste management and developing and using safer injection devices. A more radical solution is to move away from syringes and needles as delivery systems all together and toward delivery of essential agents like vaccines via needle-free methods, such as transdermal or mucosal delivery.

Mucosa is considered to be one of the largest barriers to infection in the human body. For this reason, mucosal administration of antigens (or vaccines) can theoretically be used to induce mucosal response toward systemic protection from infection at a variety of mucosal sites in the body. Mucosal routes such as oral intestinal, oral buccal, oral sublingual, nasal, ocular, pulmonary, rectal, and vaginal administration provide excellent opportunities for the delivery of a variety of dry preserved vaccines without a need for pre-delivery reconstitution. Skin vaccination also offers immunologic advantages due to vaccine targeting to antigen-presenting cells of the skin, as well as access to draining lymph nodes (Glenn et al. 2006). Micro-needle patches placed on the skin enable reliable vaccine targeting to the skin using a device that is easy to administer and is compatible with dry carbohydrate-glass formulations that require storage in a dry state (Prausnitz et al. 2009).

Currently many conventional pharmaceuticals can be stored at ambient temperatures (AT) and delivered via oral (intestinal, sublingual, and buccal), transdermal, respiratory, vaginal, and anal delivery routes without reconstitution with water before delivery, avoiding painful parenteral injection and necessity of medical personnel. To achieve needle-free delivery, the pharmaceutical industry has developed sophisticated methods and tools for production: tablets, dissolvable films, patches, suppositories, ointment, creams, and capsules (including enteric coated capsules for intestinal delivery). These methods have been broadly described in the literature (Guidice 2006, O'Hagan 2004), however none to date have been effectively applied to vaccines and other fragile biopharmaceuticals (therapeutic proteins, probiotics, etc.).

A primary reason these methods have not been used with vaccines is because conventional preservation techniques (i.e. freeze-drying and spray-drying) have failed to deliver potent ambient-temperature stable products that can survive both the harmful conditions needed for preparing devices used for needle-free delivery, and storage (including distribution) at ambient temperatures.

Drying Technologies

Drying is required for formulation of ambient-temperature stable vaccines.

Stabilization of vaccines to enable storage at room or higher temperatures (i.e. 37° C.) can be achieved in a partially dehydrated state only for a limited amount of time (several days); however, long-term stabilization of vaccines requires arresting molecular mobility to stop the degradation processes that occur during storage. It is currently recognized that one of the only ways this can be achieved is by immobilization of biologicals in carbohydrate glasses, or vitrification: the transformation from a liquid into a supercooled or supersaturated, noncrystalline, amorphous solid state, known as the "glass state." In general terms glasses are thermodynamically unstable, amorphous materials, however, they can be very stable for long periods of time because of their very high viscosity. For example, a typical liquid has a flow rate of 10 m/s compared to 10-14 m/s in the glass state.

The basic premise of this work is that the high viscosity of the glass state will arrest all diffusion-limited physical processes and chemical reactions, including the processes responsible for the degradation of biological materials. This premise is based on Einstein's theory that establishes the inverse proportionality between viscosity and molecular mobility (or diffusion coefficients of molecules). The presence of water in a sample has a strong plasticizing effect, which decreases the glass transition temperature (Tg) and thus limits stability at higher temperatures. For example, for an 80% sucrose solution, Tg is about −40° C. while the Tg of a 99% solution is about 52° C. Therefore, if specimens are to be preserved without degradation in the glass state at an ambient temperature, they must be strongly dehydrated.

Dehydration (drying) can be very damaging to vaccines and other biologicals if performed in the absence of protective, glass-forming carbohydrates (i.e. sucrose, mannitol, etc.). These molecules replace water of hydration at the surface of biological molecules, and this way protects the biologicals from destruction associated with hydration forces that arise during dehydration.

Freeze Drying

Freeze-drying (FD) has failed to deliver ambient-temperature stable vaccines.

Despite its limitations and shortcomings, freeze-drying has remained, for more than 50 years, the primary method to stabilize fragile biopharmaceuticals in the dry state. This is in part because conventional belief suggests that drying at low temperatures would be less damaging, and, in part because for many years there were no alternative drying technologies available that were scalable and maintained product integrity. Currently available lyophilized vaccines must be shipped and stored in a "cold chain" to maintain vaccine potency, deviation from which can result in incapacitating losses in vaccine titer.

Freeze-drying can also be very damaging, with lyophilization-induced injury happening both during freezing and during subsequent ice sublimation from frozen specimens at intermediate low temperatures (between −50° C. and −20° C.) at which most damaging cryochemical reactions occur.

To produce micronized powders for pulmonary or respiratory delivery, FD vaccines require milling. Although it has been demonstrated that FD measles vaccine can be micronized using a jet mill with only a small loss of activity titer (LiCalsi et al. 2001), the reported efficacy for milled freeze-dried measles vaccine is much below that for nebulized liquid-reconstituted measles vaccine (de Swart et al. 2007). As de Swart suggested (de Swart et al. 2006), this could be due to the inherently low stability of freeze-dried vaccines, which are then damaged further in the milling process.

Spray Drying

Spray-drying (SD) has failed to deliver ambient temperature stable vaccines.

Other scientific groups have avoided use of freeze-drying and turned to spray-drying (SD) in order to obtain dry microspheres suitable for respiratory delivery without involvement of a milling process, which requires special equipment and containment. Unfortunately, conventional spray-drying involves spraying (formation of small drops) of a liquid to be dried (usually water-based) into hot (typically 90° C. or above) air, which quickly evaporates water from the drops and sterilizes the material in the process. To avoid the damaging effects of high temperature, the spray-drying process should be modified to decrease the maximum temperature of the drops of vaccine during the process. This can be achieved by decreasing the temperature of the air and the drops simultaneously, and reducing the diameter of the drops of vaccine that that are produced by the spraying nozzle.

Aktiv-Dry LLC has been the leading group to use a spray-drying approach for preparation of measles vaccine for pulmonary delivery. Aktiv Dry has used supercritical $CO_2$ to decrease the diameter of drops sprayed into air simultaneously with decrease of the air temperature. They have reported that the lower temperature SD process allows them to produce micronized vaccines with good activity after drying. However, their vaccines are not stable at ambient temperatures and lose more than 0.5 logs (>70%) of activity after only one week storage at 37° C., which is worse than the stability of measles vaccine currently produced by freeze-drying.

There are fundamental reasons (some of them are addressed below) explaining why it is very difficult and may be even impossible to achieve both good initial yield and stability of live vaccines that have been dried via SD. For one, it is very difficult to remove water from spray-dried particles which contain sugars or other glass forming molecules if during spray drying the temperature inside drops did not increase above the vaccine damaging level. This is because the rate of evaporative drying is limited by water mobility inside the drop and it becomes very slow when the drop loses most of its water and becomes very viscous. It is well known that the characteristic time (t) of the diffusion relaxation in the drop with diameter (d) is about $t=d^2/D$, where D is the water diffusion coefficient and d is the drop diameter. In dilute solutions, $D=10^5$ sm2/sec and t=0.1 sec for small drops with diameter d=10 However, in drops containing concentrated solutions (syrups), it will greatly increase with a decrease of molecular mobility and diffusion coefficient (D). In concentrated syrups, D is larger than $10^5$ sm2/sec by many orders of magnitude, which makes t many orders of magnitude higher than the typical spray-drying process time. Thus, a significant amount of water, resulting in a high mobility, will remain in the drops after spray-drying if the drops contain sugars or other glass forming additives required to protect the vaccine from the desiccation stress until spray drying is performed at temperatures that are substantially higher than the glass transition temperatures of protective carbohydrates in the drops. Spay drying at high temperatures normally inactivate vaccines and other biopharmaceuticals. Conventionally, spray drying was used as a disinfective process for milk and many other products. Thus, during spray-drying, decreasing the air temperature is necessary to avoid vaccine inactivation; yet, that will result in a higher concentration of water remaining in the material after the drying process, which will negatively affect stability during subsequent storage at ambient temperatures.

Both spray-drying and freeze-drying had been used for more than 50 years and attempts to apply these technologies to produce ambient temperature stable live attenuated vaccines and other fragile biopharmaceuticals had been unsuccessful.

A scalable Foam Drying under vacuum technology as described in U.S. Pat. No. 5,766,520 was introduced by Dr. Bronshtein as an alternative to freeze-drying and spray drying to produce thermostable biopharmaceuticals. In other words, foam drying was introduced to scale up the film drying. This foam drying technology called "Preservation by Foam Formation (PFF)" has many drawback including uncontrollable eruptions, difficulties of the process control and reproducible execution.

Preservation by Vaporization (PBV)—State of the Art of Foam Drying

In 2004, Dr. Bronshtein proposed Preservation by Vaporization (PBV) technology, during which a partially frozen material (slush) sublimates, boils and evaporates simultaneously (PCT Patent Application WO/2005117962). PBV is scalable, easy to control and reproduce, and has minimum splashing. Preliminary studies have illustrated the unique benefits of PBV technology, including:

higher activity titer after drying and thermostability during subsequent storage at ambient temperature (increased shelf-life);

eliminates the need for using a "cold chain";

allows subsequent mechanical and jet milling (micronization) with minimum activity loss;

allows drying of vaccines encapsulated in gel microparticles for better intestinal delivery, avoiding the need for pre-delivery reconstitution with water; and allows short-term (several hours) stability at 60° C. to 90° C. that is useful for encapsulation of dry powders in dissolvable polymeric patches for transdermal delivery and in quick dissolve tablets and films for oral delivery.

PBV is faster and less expensive than freeze-drying for producing thermostable vaccines, and PBV potentially allows for execution of barrier aseptic drying because during the PBV primary drying step the water vapor pressure above the specimen is 20 or more times higher than that during freeze-drying because PBV is performed at higher temperatures.

SUMMARY OF INVENTION

Technical Problem

There has yet to be described ambient-temperature stable compositions and related methods for needle-free delivery of sensitive biopharmaceuticals including vaccines and probiotics.

Conventional vaccine delivery platforms require cold chain storage up until the point of delivery. There has yet to be described an anhydrous delivery platform for sensitive biopharmaceuticals that does not require cold chain storage throughout distribution and shelf-life.

There has yet to be described an ambient temperature stable delivery platform for such sensitive biopharmaceuticals that does not require reconstitution in water.

There is a need for needle-free delivery of sensitive biopharmaceuticals, such as via dissolvable films, microneedle patches, and similar delivery devices. To manufacture such delivery devices there is a need for polymeric compositions containing ambient-temperature stable biopharmaceuticals.

It is difficult to make water-soluble polymeric compositions containing carbohydrate-glass powders. Sensitive biopharmaceuticals can be encapsulated in carbohydrate-glass particles, or powders, using freeze drying, spray drying, and foam drying techniques, however, the carbohydrate-glass is subject to solubility in water resulting in difficulty to combine the powder and water-soluble polymeric films. For example, dissolving a water-soluble polymer in aqueous solution for forming such a film or micro-needle patches is not suitable since the aqueous solution will also diffuse or dissolve the carbohydrate-glass particles, resulting in loss of stability or bio activity loss.

Solution to Problem

Integrating water-soluble polymeric substrates and powder comprising carbohydrate sugar particles containing ambient temperature stable biopharmaceuticals, such as vaccines or probiotics, can be accomplished using polymers that are soluble in both water and an organic solvent. Such a combination works if the carbohydrate-glass, is insoluble in the organic solvent.

In an embodiment, a method for forming polymeric compositions containing ambient-temperature stable biopharmaceuticals comprises: obtaining an amount of ambient-temperature stable biopharmaceuticals micronized for delivery; dissolving one or more polymeric excipients and one or more plasticizers in a volatile organic solvent to form a polymer solution; introducing the glass particles containing the ambient-temperature stable biopharmaceuticals into the polymer solution to form a mixture; and evaporating the organic solvent from the mixture.

In another embodiment, a polymeric composition containing ambient-temperature stable biopharmaceuticals comprises: an amorphous substrate comprising a polymeric excipient and a plasticizer; and an amount of ambient-temperature stable encapsulated biopharmaceuticals embedded within the substrate; wherein the polymeric excipient is soluble in both water and a volatile organic solvent; and wherein said ambient-temperature stable encapsulated biopharmaceuticals are not soluble in said organic solvent.

In yet another embodiment, a medical delivery device for needle-free delivery of biopharmaceuticals comprises: one or more of: a vaccine agent or a probiotic encapsulated in carbohydrate-glass particles; the carbohydrate-glass particles being embedded in an amorphous polymer substrate; wherein said amorphous polymer substrate is soluble in both water and organic solvent.

Advantageous Effects of Invention

The compositions and delivery devices as described herein can be used to deliver sensitive biopharmaceuticals without the use of needles, thereby aiding in the reduction of needle related problems as described above.

The compositions and delivery devices herein do not require reconstitution in water. Thus, the invention can be used in regions of the World where clean water is not readily available.

The compositions and delivery devices described herein do not require cold chain for storage and distribution. As such, the compositions can be distributed with a much lower cost compared to conventional vaccines which require cold chain storage.

Hydroxypropyl cellulose is soluble in both water and acetone. Carbohydrate-glass particles of thermostable powers are insoluble in acetone. As such, by first encapsulating sensitive biopharmaceuticals in carbohydrate-glass the resulting powders can be combined with hydroxypropyl cellulose in acetone, and the acetone evaporated, to form a water-soluble polymeric composition containing thermostable biopharmaceuticals.

It was discovered that powders derived from PBV containing carbohydrate-glass particles and embedded biopharmaceuticals were not dissolved in acetone, a volatile organic solvent, and activity of embedded biopharmaceuticals remained high after reconstitution. Accordingly, it was concluded that diffusion of solvent into the particles was limited or nonexistent based on activity results.

It is important to control temperature when working with sensitive biopharmaceuticals. If the temperature is too warm, or too cold, activity of the can be lost and the biopharmaceuticals damaged. The method described herein is advantageous at least for the reason that during manufacturing, temperature can be sufficiently controlled to reduce or eliminate loss of activity caused by exposure to extreme temperatures.

When using a foam drying technique, and more preferably PBV, for obtaining ambient-temperature stable biopharmaceuticals, activity of sensitive biologicals can be preserved at ambient temperatures for many months, thus providing long-term stability.

DESCRIPTION OF EMBODIMENTS

Definitions

For purposes of this invention, the term "biopharmaceuticals" is used herein to describe encapsulated sensitive biopharmaceuticals including (i) vaccine agents, such as but no limited to: killed micro-organisms, including: rabies, influenza, cholera, bubonic plague, polio, hepatitis A, and HIV; live attenuated microorganisms, including: yellow fever, measles, rubella, mumps, typhoid, influenza, RSV, H5N1, cholera, bubonic plague, polio, hepatitis A; inactivated toxic compounds, including: tetanus, and dipthera; and subunit proteins, including: surface proteins of hepatitis B virus, and viral major capsid protein, and the hemagglutinin and neuraminidase subunits of influenza virus, and (ii) probiotics, such as but not limited to: *L. rhamnosus; L. jensenii*; and *L. crispatus*.

The term "ambient-temperature stable" is used herein to describe the stability of sensitive biopharmaceuticals at ambient temperature. In the scope of this application we will consider any temperature between −20° C. and +40° C. as an ambient temperature. We will call a formulation of biopharmaceutical ambient temperature stable if the biopharmaceutical will have less than 0.5 logs (or 66%) of the activity loss after storage above 37° C. during a period of at least two months storage at 25° C. (room temperature) or lower ambient temperatures during a period of at least two years. Normally stability of biopharmaceuticals immobilized inside carbohydrate glasses increases with decreasing storage temperature. For this reason, it is difficult to achieve required stability at 25° C. and 37° C. Accordingly, ambient temperature stable biopharmaceuticals also are often referred to as "thermostable" biopharmaceuticals. In the scope of this application we will consider thermostable and ambient temperature stable biopharmaceuticals to be interchangeable.

The term "micronized" is used herein to describe a substance which is milled or otherwise processed to yield particles having a size of 50 microns or less, such particles in plurality forming a micronized powder.

The term "biocompatible" is used herein to describe the quality of not having toxic or injurious effects on biological systems.

The term "polymeric excipient" is used herein to describe a polymer formulated alongside the active ingredient of a pharmaceutical composition.

The term "bi-soluble" is used herein to describe solubility in both water (aqueous solution) and a volatile organic solvent.

The term "plasticizer" is used herein to describe additives that increase the plasticity of the polymer in the solid state.

The term "organic solvent" is used herein to describe carbon-based substances that are capable of dissolving the polymer.

The term "polymer solution" is used herein to describe one or more polymers, plasticizers, and other materials dissolved in a liquid solvent medium.

The term "foam drying" is a general term used herein to describe various drying techniques for obtaining preserved biopharmaceuticals, including "preservation by foam formulation (PFF)" as described in U.S. Pat. No. 5,766,520; and "preservation by vaporization (PBV)" as described in WO 2005/117962

The term "preservation by vaporization (PBV)" describes the current state of the art method for preserving sensitive biological.

The term "carbohydrate-glass" is used herein to describe an amorphous solid carbohydrate matrix including one or more carbohydrates, generally sugars. The matrix may further include amino acids, salts, surfactants and polymers that were dissolved in preservation solutions before drying.

The term "amorphous polymer substrate" is used herein to describe a polymer substrate that lacks the long-range order characteristic of a crystal.

The term "water-soluble film" or "dissolvable film" is used herein to describe a solid comprising one or more thin layers of a water soluble polymeric composition. Typically the thickness of the dissolvable films used to deliver biopharmaceuticals is between 1 and 100 microns.

The term "micro-needle patch" is used herein to describe a solid polymeric patch containing micro needles that pierce into the skin upon application similar to that of a regular bandage. The micro needles dissolve in the skin, release and deliver the therapeutic.

The term "delivery device" is a general term used herein to describe a device for delivering a therapeutic. For example, dissolvable films and patches are the delivery devices.

In accordance with aspects of the invention, it is a primary objective to form a water-soluble polymeric composition containing ambient-temperature stable biopharmaceuticals for administration to a patient. The composition can be manufactured in different forms including dissolvable films, micro-needle patches, or similar medical delivery devices. However, it is important that during manufacture of such devices, the contained ambient-temperature stable biopharmaceuticals, such as carbohydrate-glass vaccine powders or probiotic powders, must not be dissolved or activity thereof should not be destroyed. Accordingly, because carbohydrate-glass powders are soluble in water, an organic solvent is preferred to be used when making a polymer solution. In this regard, the carbohydrate-glass powder can be mixed into a suspension with the anhydrous polymer solution in which the powder remains in solid phase such that sensitive biological agents remain protected in an encapsulating particle.

To achieve this goal, and to effectively formulate dissolvable films and micro-needle patches containing dry vaccine powders, novel mixtures are suggested herein comprising a bi-soluble polymer such as, for example, hydroxypropyl cellulose (HPC) with a plasticizer such as, for example, triacetin, dissolved in an organic solvent such as, for example, acetone. Because the bi-soluble polymer is soluble in both water and organic solvent, an organic solvent can be used to dissolve the polymer and plasticizer to form a polymer solution and the carbohydrate-glass powder can be suspended therein without harm to the encapsulated biopharmaceuticals. Upon evaporation of the organic solvent, the resulting polymeric composition contains carbohydrate-glass powder and protected biopharmaceuticals therein, which can be used to manufacture a delivery device, such as a dissolvable film or micro-needle patch.

Figure 1:
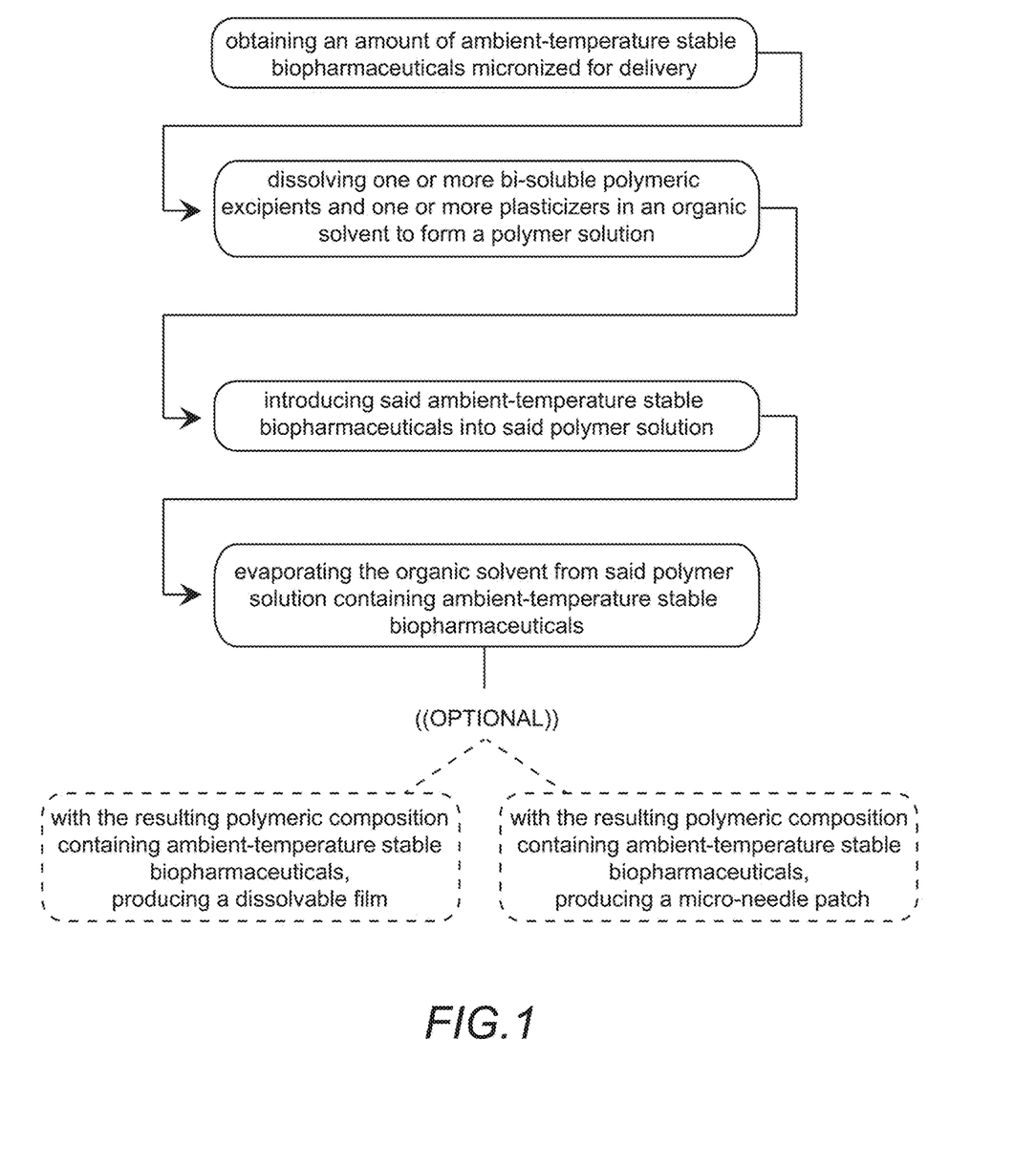
FIG. 1 illustrates a general method for forming polymeric compositions containing ambient-temperature stable biopharmaceuticals.
Figure 2:
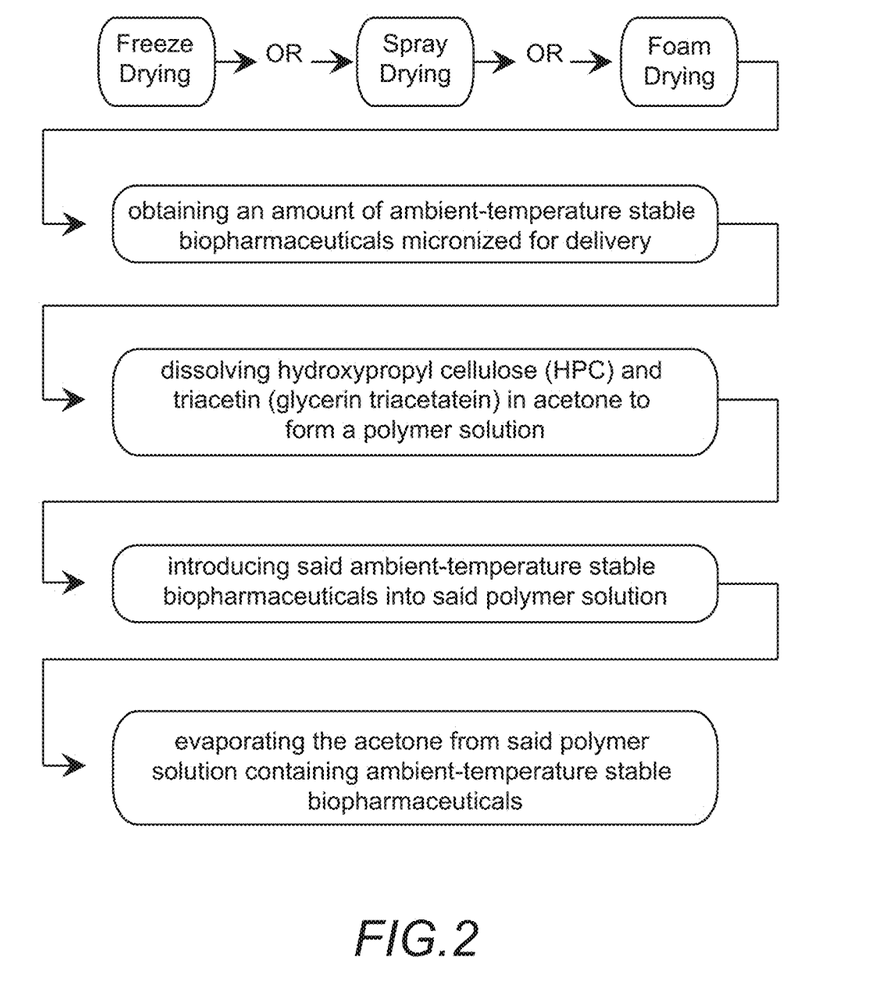
FIG. 2 illustrates a method for forming polymeric compositions containing ambient-temperature stable biopharmaceuticals in accordance with one preferred example.
Figure 3:
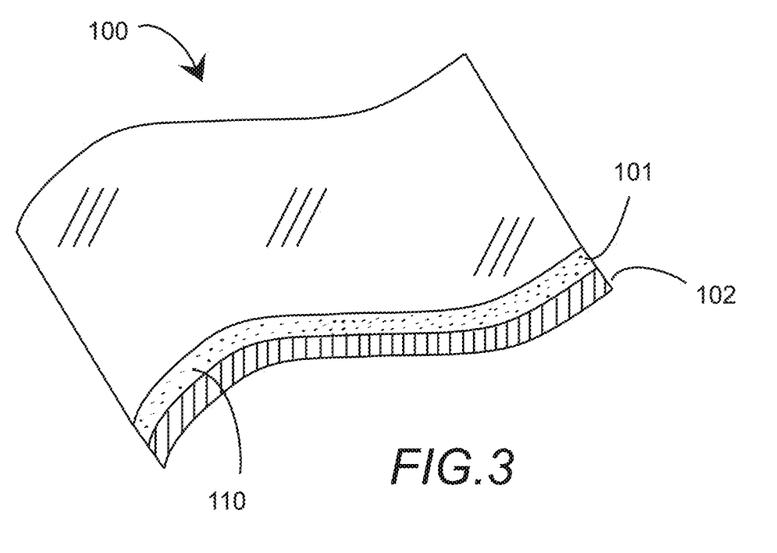
FIG. 3 illustrates a delivery device for the delivery of sensitive biopharmaceuticals to a patient; the delivery device includes a dissolvable film containing ambient-temperature stable biopharmaceuticals.
Figure 4:
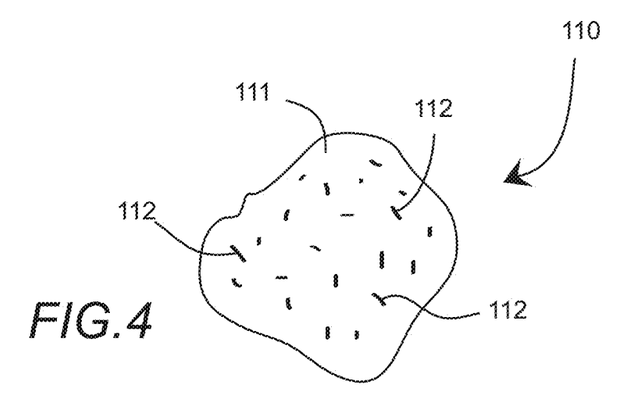
FIG. 4 illustrates a micronized ambient-temperature stable biopharmaceutical, in the form of a particle, having at least one vaccine agent or probiotic encapsulated in a carbohydrate-glass.
Figure 5:
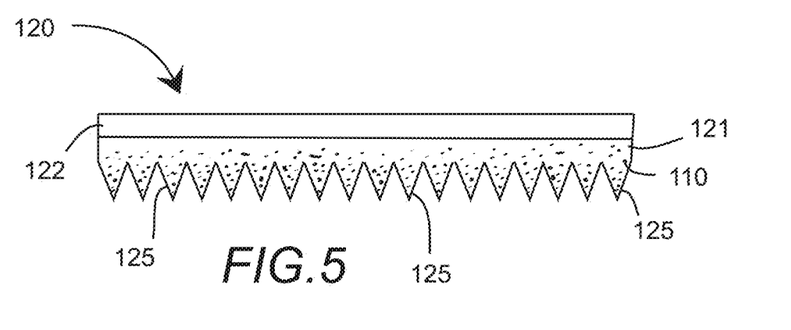
FIG. 5 illustrates a delivery device for the delivery of sensitive biopharmaceuticals to a patient; the delivery device includes a micro-needle patch containing ambient-temperature stable biopharmaceuticals.

Although various examples are given, it should be generally understood that any polymer that is biocompatible and bi-soluble, or soluble in both water and volatile organic solvent, can be used, along with any suitable plasticizer known to those having skill in the art, with the same or similar methods as described herein to achieve similar results. The claimed invention is not intended to be limited by the express examples herein. Rather, these examples are being offered in order to illustrate one preferred embodiment.

Now turning to the drawings, FIG. 1 illustrates a general method for forming polymeric compositions containing ambient-temperature stable biopharmaceuticals. The general method comprises, in any order, (i) obtaining an amount of ambient-temperature stable biopharmaceuticals micronized for delivery; (ii) dissolving one or more bi-soluble polymeric excipients and one or more plasticizers in an volatile organic solvent to form a polymer solution; (iii) introducing the ambient-temperature stable biopharmaceuticals into the polymer solution and suspending therein; and (iv) evaporating the organic solvent from the polymer solution containing ambient-temperature stable biopharmaceuticals.

Using the composition derived from the general method above, one or more optional processing steps may include: producing a dissolvable film; or producing a micro-needle patch. The manufacture of both dissolvable films and micro-needle patches from aqueous solutions by water casting are known in the art, and the manufacture of these from anhydrous polymeric suspensions would be similar, however using a novel polymer composition containing ambient-temperature stable biopharmaceuticals as described herein.

In addition to these delivery devices, the composition can also be used as a coating for an off the shelf personal medical device, such as a bandage, a tampon, or a vaginal ring, among others.

It should be noted that there were many unsuccessful attempts obtaining ambient-temperature stable biopharmaceuticals via conventional drying processes, such as freeze drying and spray drying. In many studies it was shown that foam drying provide activity and stability superior to that which could be obtained by freeze-drying and spay dying. Foam drying, such as preservation by foam formulation (PFF), or preservation by vaporization (PBV), is preferred. And more particularly, PBV is preferred due to the enhanced bioactivity stabilization that has been shown using this process. However, if successful any process which preserves sensitive biopharmaceuticals can be used to obtain the ambient-temperature stable biopharmaceutical powders used in the embodiments herein.

If needed, a milling process, such as by using a jet mill or ball milling, can be implemented to powders for micronizing to the desired particle size.

FIG. 2 illustrates a method for forming polymeric compositions containing ambient-temperature stable biopharmaceuticals in accordance with one preferred example. Here, one of freeze drying, spray drying, or foam drying is used to obtain ambient-temperature stable biopharmaceutical powder, and preferably PBV is used. The powder is micronized, such as by using a jet mill or other known micronizing process to achieve the desired particle size. A preferred biocompatible bi-soluble polymer, hydroxypropyl cellulose (HPC), is combined with a preferred plasticizer, triacetin, and dissolved in acetone to form a polymer solution. The ambient-temperature stable biopharmaceutical powder is introduced and suspended into the polymer solution. The acetone is subsequently evaporated to yield a polymeric composition containing ambient-temperature stable biopharmaceuticals. The resulting composition is soluble in water, and therefore can be used for the manufacture of dissolvable films or micro-needle patches.

FIG. 3 illustrates a delivery device for the delivery of sensitive biopharmaceuticals to a patient; the delivery device includes a dissolvable film containing ambient-temperature stable biopharmaceuticals. The dissolvable film 100 comprises at least one layer (two layers are shown 101; 102, respectively). A first layer 101 comprises a polymeric composition containing ambient-temperature stable biopharmaceuticals as described above. The first layer substantially consists of a water-soluble polymer matrix and a plurality of carbohydrate-glass particles 110 suspended therein. The carbohydrate-glass particles encapsulate a plurality of vaccine agents or probiotics for preservation. A second layer of the film 102 can comprise a polymer substrate, with or without preserved biopharmaceuticals, and optionally with a differentiated polymer matrix than that of the first layer, such as a second polymer matrix with additional crosslinking or other material characteristics for enhanced delivery, sustained delivery, or other benefits.

FIG. 4 illustrates a micronized ambient-temperature stable biopharmaceutical, in the form of a particle 110, having at least one vaccine agent or probiotic 112 encapsulated in a carbohydrate-glass 111.

FIG. 5 illustrates a delivery device for the delivery of sensitive biopharmaceuticals to a patient; the delivery device includes a micro-needle patch 120 containing ambient-temperature stable biopharmaceutical containing particles 110. The micro-needle patch comprises a plurality of micro-needles 125 formed from dissolvable polymer containing particles 110. An optional multi-layer embodiment, similar to that of the film in the above example, can be practiced, wherein the micro-needle patch comprises a first layer 121 and a second layer 122 adjacent to the first layer. In this regard, the optional first and second layers may comprise differentiating properties, such as with or without particles, with more or less cross-linking, more or less plasticizer, or other material variations known by those with skill in the art to yield differentiating material properties.

To further describe a preferred embodiment, the following examples are provided:

Example 1 Thermostabilization of Probiotic Bacteria Using PBV

In this example, "Thermostable Vaginal Probiotic Microbicides" were formulated. One goal was to investigate the application of live probiotic bacterial microbicides against sexually transmitted diseases. The strategy was to use probiotics to occupy the vaginal epithelium and provide a long lasting protective environment against HIV, BV, and other STIs. Another goal of this work is formulation of potent multi strain thermostable probiotic vaginal topical microbicides (TPVM) that can be delivered using conventional thin film technology. It was first demonstrated that PBV preserved vaginal bacterial probiotics could be stable for at least 11 months 37° C. and 1 hour at 70° C. (see Table 1.1). This allowed effective encapsulation of these bacteria in thin polymeric films for delivery to vaginal (cervical) epithelium.

TABLE 1.1

Survival of PBV bacteria ($10^8$ CFU/ml) at 37° C. and 70° C.

| Treatment | Activity of L. rhamnosus | Activity of L. jensenii | Activity of L. crispatus |
|---|---|---|---|
| Before drying | | | |
| Form. 1 | 139 ± 17 | 118 ± 12 | 95 ± 28 |
| Form. 2 | — | 137 ± 12 | 94 ± 9 |
| Form. 3 | 150 ± 15 | 119 ± 14 | 93 ± 14 |
| After drying | | | |
| Form. 1 | 93 ± 1.5 | 110 ± 15 | 70 ± 12 |
| Form. 2 | 77 ± 8 | 106 ± 12 | 65 ± 13 |
| Form. 3 | 103 ± 14 | 126 ± 22 | 67 ± 8 |
| After 1 hour at 70° C. | | | |
| Form. 1 | 81 ± 6 | 101 ± 8 | 67 ± 8 |
| Form. 2 | 56 ± 21 | 85 ± 11 | 50 ± 3 |
| Form. 3 | 109 ± 3 | 104 ± 19 | 56 ± 9 |
| After 3 months at 37° C. | | | |
| Form. 1 | 78 ± 6 | 116 ± 20 | 52 ± 9 |
| Form. 2 | 69 ± 3 | 49 ± 29 | 37 ± 6 |
| Form. 3 | 15 ± 6 | 54 ± 9 | 53 ± 15 |
| After 6 months at 37° C. | | | |
| Form. 1 | 49 ± 7 | 31 ± 7 | 52 ± 12 |
| Form. 2 | 31 ± 8 | 47 ± 3 | 25 ± 3 |
| Form. 3 | 3.4 ± 0.6 | 23 ± 4 | 40 ± 7 |
| After 11 months at 37° C. | | | |
| Form. 1 | 76 ± 7 | 42 ± 3 | 33 ± 5 |
| Form. 2 | 2.4 ± 1.7 | 31 ± 3 | 0 |
| Form. 3 | 1 ± 0.4 | 4.5 ± 1 | 0 |
| After 11 months at RT | | | |
| Form. 1 | 113 ± 10 | 86 ± 15 | 55 ± 19 |
| Form. 2 | 100 ± 16 | 86 ± 10 | 36 ± 11 |
| Form. 3 | 68 ± 6 | 94 ± 16 | 2.5 ± 2.5 |

Here, three preservation solutions (PS) were formulated to protect bacteria during PBV drying and subsequent storage at ambient temperatures. PS 1: comprised of 30% sucrose and 10% methylglucoside; PS 2: comprised of 30% sucrose and 10% mannitol; PS 3: comprised of 30% sucrose and 10% isomalt.

A gentle PBV drying protocol was developed to stabilize probiotic bacteria (*L. crispatus*, *L. jensenii* and *L. rhamnosus*) at ambient temperatures.

For all three bacteria, it was demonstrated that: more than 70% of the bacteria survived after drying; more than 70% of the bacteria survived after 60 minutes of post-drying equilibration at 70° C.; more than 50% of the bacteria survived after 3 months of storage at 37° C.; more than 50% of the bacteria survived after 11 months of storage at room temperature; and more than 30% of the bacteria survived after 11 months of storage at 37° C. in the formulation containing methylglycoside (PS1). See Table 1.1.

Figure 6A:
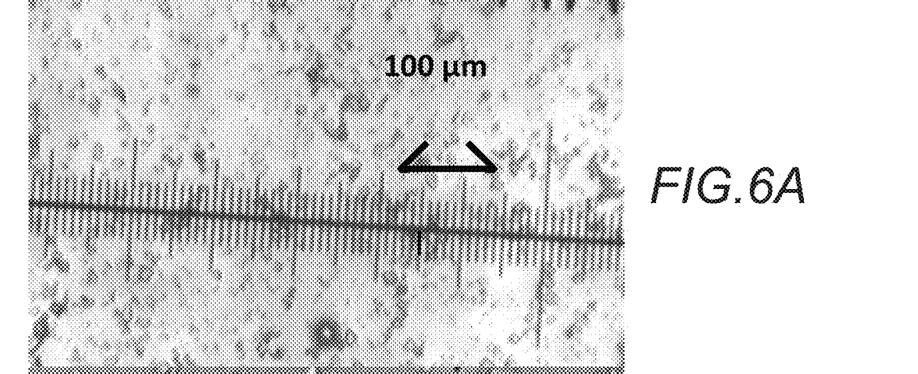
FIG. 6A shows ambient-temperature stable biopharmaceutical powder under a microscope at a first magnification.
Figure 6B:
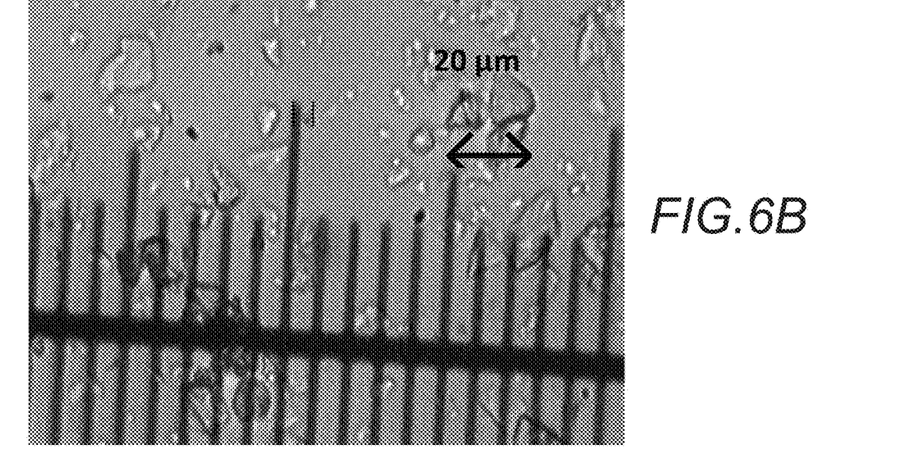
FIG. 6B shows ambient-temperature stable biopharmaceutical powder under a microscope at a first magnification; the particles are shown having a diameter of about 20 microns.

It was also demonstrated that micronization of dry preserved bacteria using FPS Jet Mill at injector pressure of 60 psi did not damage bacteria and allows decreasing size of dry sugar particles to about 20µ or less as is seen from FIGS. 6(A-B).

These thermostable micronized probiotic powders for development of dissolvable films containing the probiotics (see below).

Example 2. Solubility of Different Polymers and Plasticizers in Acetone

Studies were performed to determine compatibility between many organic solvents and plasticizers with the carbohydrate-coated lactobacilli and other PVB preserved biologics. Solvents looked at included acetone, ethanol, dichloromethane, and ethyl acetate, all of which are commonly used as volatile solvents for preparation of polymeric water-dissolvable films and other devices. Acetone was chosen as the preferred organic solvent for use in film or patches formulation development due to its compatibility with carbohydrate-glass particles and low toxicity. It was found that PBV-preserved bacteria could be kept in acetone at 37° C. for >24 hours with no loss in bacterial activity. The same was found to be valid for triacetin, a reason for which it could be a preferred acetone-soluble plasticizer in these formulations (see table. 2.1). It was also found that of the many potential polymers that could be used to produce patched and films, hydroxypropyl cellulose (HPC) was the only one that dissolved in acetone (Table 2.2).

TABLE 2.1

Solubility study results for different plasticizers in commonly used organic solvents

| Plasticizer | Concentration (w/v) | Acetone | Ethanol | Dichloromethane | Ethyl acetate |
|---|---|---|---|---|---|
| PEG 400 | 1% | + | + | + | + |
|  | 3% | + | + | + | + |
| Sorbital | 1% | − | − | − | − |
|  | 3% | − | − | − | − |
| Propylene Glycol | 1% | + | + | + | + |
|  | 3% | + | + | + | + |
| Glycerin | 1% | − | + | − | − |
|  | 3% | − | + | − | − |
| Triacetin | 1% | + | + | + | + |
|  | 3% | + | + | + | + |
| Pluronic F127 | 1% | + | + | + | + |
|  | 6% | + | P | + | + |

TABLE 2.1-continued

Solubility study results for different plasticizers in commonly used organic solvents

| Plasticizer | Concentration (w/v) | Acetone | Ethanol | Dichloromethane | Ethyl acetate |
|---|---|---|---|---|---|
| PEG 4000 | 1% | + | P | + | + |
|  | 6% | + | P | + | P |

"+" means dissolved;
"−" means not dissolved;
"P" means the excipient precipitated out when placed overnight at room temperature after solubilization with the help of 3 h sonication.

TABLE 2.2

Solubility study results for different polymers in commonly used organic solvents

| Polymer | Concentration (w/v) | Acetone |
|---|---|---|
| PVP K90 | 1% | − |
|  | 6% | − |
| Pullulan | 1% | − |
|  | 6% | − |
| HPMC E5 | 1% | − |
|  | 6% | − |
| HPC | 1% | + |
|  | 6% | + |
| HEC | 1% | − |
|  | 6% | − |
| Methyl Cellulose | 1% | − |
|  | 6% | − |
| CMC-Na | 1% | − |
|  | 6% | − |
| PVA | 1% | − |
|  | 6% | − |

"+" means dissolved;
"−" means not dissolved;

Example 3. Placebo Film Formulation Development

The acetone-based polymer solution was used as the film base to prepare several film prototypes (Table 3.1). The film prototypes were manufactured by creating a uniform polymer solution which was cast onto a glass substrate attached to the hot surface of an automatic film applicator (ELCOMETER® 4340) using the mini-applicator doctor blade. None of the evaluated prototypes tested resulted in acceptable film properties including manufacturability, mechanical strength, and appearance. Manufacturing parameters were modified with respect to casting substrate used, drying time, and temperature. It was found that "Formulation 4" with modified manufacturing parameters could be used to achieve an acceptable film platform. Once the optimal placebo formulation was established, the bacteria were loaded into the film.

TABLE 3.1

The tested formulations during the optimization of placebo films.

| Formulation 1 | | Formulation 2 | | Formulation 3 | |
|---|---|---|---|---|---|
| HPC | 0.8 g | HPC | 0.8 g | HPC | 0.8 g |
| PEG400 | 0.2 g | PEG400 | 0.4 g | PEG400 | 0.6 g |
| Acetone | 10 ml | Acetone | 10 ml | Acetone | 10 ml |

TABLE 3.1-continued

The tested formulations during the optimization of placebo films.

| Formulation 4 | | Formulation 5 | | Formulation 6 | |
|---|---|---|---|---|---|
| HPC | 0.8 g | HPC | 0.8 g | HPC | 0.8 g |
| Triacetin | 0.2 g | Triacetin | 0.4 g | Triacetin | 0.6 g |
| Acetone | 10 ml | Acetone | 10 ml | Acetone | 10 ml |
| Formulation 7 | | Formulation 8 | | Formulation 9 | |
| HPC | 0.8 g | HPC | 0.8 g | HPC | 0.8 g |
| PEG 4000 | 0.2 g | PEG 4000 | 0.4 g | PEG 4000 | 0.6 g |
| Acetone | 10 ml | Acetone | 10 ml | Acetone | 10 ml |
| Formulation 10 | | Formulation 11 | | Formulation 12 | |
| HPC | 0.8 g | HPC | 0.8 g | HPC | 0.8 g |
| F127 | 0.2 g | F127 | 0.4 g | F127 | 0.6 g |
| Acetone | 10 ml | Acetone | 10 ml | Acetone | 10 ml |

Figure 7:
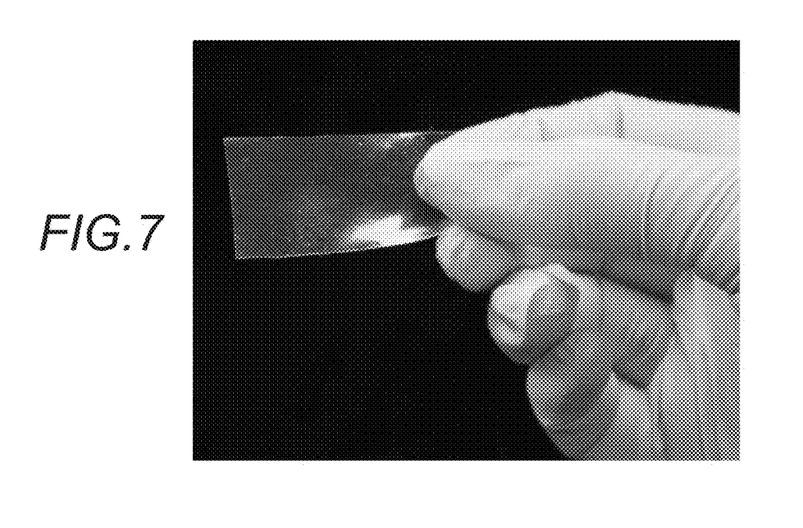
FIG. 7 shows a dissolvable film in accordance with an embodiment.

Example 4. Preparation of the HPC Film Containing Micronized Probiotic Powder The films, as shown in FIG. 7, were prepared by casting "formulation 4" from Example 3 mixed with powder of PBV-preserved *L. jensenii* on a thin film applicator and subsequent drying in a vacuum oven at 70° C. Activity of *L. jensenii* bacteria after the solvent casting film preparations in this experiment is shown in Table 4.1 below.

TABLE 4.1

Activity of *L. jensenii* bacteria after the solvent casting film preparations.

| Treatment | Activity of *L. jensenii* ($10^8$ CFU/ml) |
|---|---|
| Before PBV drying with PS3 | 119 ± 14 |
| After PBV drying with PS3 | 126 ± 22 |
| After casting on a thin film applicator onto a substrate (A) | 119 ± 5 |
| After drying in a vacuum oven at 70° C. (C) | 142 ± 13 |

Example 5: Placebo Film Formulation Development by Hot Melt Extrusion Technique As a second manufacturing option in order to limit exposure of the bacteria to aqueous medium, the use of Hot Melt Extrusion (HME) technique was evaluated. Initial studies have focused on development of a placebo prototype which could be manufactured with limited exposure to excessive high temperature. To this end Polyethylene oxide (PEO) was identified as the polymer of choice for initial prototype development work. The plasticizers PEG 400 or Glycerin were also used. Prototype formulations to date are listed in Table 5.1. For these initial formulations HME (MiniLab HAAKE®) parameters were maintained constant for the six formulations. The temperature was set to 90° C., the screw rate to 180 rpm, feeding time was 15 min and mixing time was 15 min. The polymer and the plasticizer were hand fed into the HME throughout the 15 min period. The mixture was constantly mixed until the gate was opened and was released in a ribbon form. The ribbon was immediately transferred to the roller to form the desired film shape. Optimization of film appearance and manufacturability is ongoing.

TABLE 5.1

The tested formulations during the optimization of placebo films.

| Formulation 1 | | Formulation 2 | | Formulation 3 | |
|---|---|---|---|---|---|
| PEO | 4.5 g | PEO | 3.6 g | PEO | 4.5 g |
| PEG400 | 1.5 g | PEG400 | 2.4 g | Glycerin | 1.5 g |
| Ratio | 3:1 | Ratio | 3:2 | Ratio | 3:1 |

| Formulation 4 | | Formulation 5 | | Formulation 6 | |
|---|---|---|---|---|---|
| PEO | 3.6 g | PEO | 4.5 g | PEO | 3.6 g |
| Glycerin | 2.4 g | PEG300 | 1.5 g | PEG300 | 2.4 g |
| Ratio | 3:2 | Ratio | 3:1 | Ratio | 3:2 |

Example 6: Development of Bacteria-Loaded Films by Hot Melt Extrusion Technique The film containing thermostable bacteria (up to 70° C.) requires a relatively low humidity environment during the manufacturing and storage process in order to protect the sugar coating of the bacteria. To limit the aqueous contents in the thin film, hot melt extrusion (HME) manufacturing technique was evaluated in this study. Commonly used polymers with different melting points and thermal behaviors were chosen for study in this evaluation and are shown in Table 6.1.

TABLE 6.1

The commonly used polymers with different melting points and thermal behaviors

| Polymer | Melting point (° C.) | Description |
|---|---|---|
| Hydroxypropylmethyl cellulose (HPMC) | 190-200 | Browns at 190° C. and chars at 200° C. |
| Hydroxyethyl cellulose (HEC) | 135-140, 280 | Softens at 135-140° C., decomposes at 280° C. |
| Sodium carboxymethyl cellulose (NaCMC) | 227, 252 | Browns at 227° C. and chars at 252° C. |
| Polyvinyl alcohol (PVA) | 228, 180-190 | 228° C. (fully hydrated grade), 180-190° C. (partially hydrated grade) |
| Polyvinyl pyrrolidone (PVP-K90) | 150 | Softens at 150° C. |
| Hydroxypropyl cellulose (HPC) | 260-270 | Soften at 130° C. |
| Polyethylene oxide (PEO) Hot Melt Extrusion (HME) technique | 65-70 | Soften at 60° C. |

Due to the low melting point of polyethylene oxide (PEO) it was chosen as the film forming polymer for the development of the placebo formulation. PEG 400 and glycerin were selected as the plasticizers in the formulation. HME (Mini-Lab HAAKE®) parameters remained constant for all trials. The temperature was maintained as 90° C., and the speed of screws was set at 180 rpm. Additionally, the feeding time was controlled within 15 min and the mixing time fixed at 15 min. The polymer and the plasticizer were hand fed into the HME, and the mixture was allowed to mix until the gate was open. Then, the mixture was extruded through a die in a ribbon form. The ribbon was immediately transferred to a roller to make a film. The results of the 3 formulations are presented in Table 6.2 and Table 6.3.

TABLE 6.2

Development of placebo film formulations using HME

| Formulation 1 | | Formulation 2 | | Formulation 3 | |
|---|---|---|---|---|---|
| PEO | 4.5 g | PEO | 3.6 g | PEO | 4.5 g |
| PEG400 | 1.5 g | PEG400 | 2.4 g | Glycerin | 1.5 g |
| Ratio | 3:1 | Ratio | 3:2 | Ratio | 3:1 |

TABLE 6.3

The performance of each formulation

| Formulation | Parameter setting | Commentary |
|---|---|---|
| 1 | 90° C.; 180 rpm; 15 min | 1.32 g yield. Film is softer compared to 100% PEO. |
| 2 | 90° C.; 180 rpm; 15 min | 1.86 g yield. Film is softer compared to 100% PEO. However, the film was found to be very oily. |
| 3 | 90° C.; 180 rpm; 15 min | 1.66 g yield. Inadequate mixing of PEO and glycerin. The film was very soft. |

Continuous optimization studies were conducted to improve the texture properties of the film and to reduce the heat during the manufacturing process. The temperature was decreased to 70° C., and the speed of screws was set at 180 rpm. Feeding time was 15 min and mixing time was 10 min. The polymer and the plasticizer were hand fed into the HME, and the mixture was allowed to mix until the gate was open. Then, the mixture was extruded through a die in a ribbon form. The ribbon was immediately transferred to a roller to make a film. The results of three formulations are presented in Table 6.4 and Table 6.5.

TABLE 6.4

Development of placebo film formulations using HME

| Formulation 4 | | Formulation 5 | | Formulation 6 | |
|---|---|---|---|---|---|
| PEO | 3.0 g | PEO | 3.0 g | PEO | 3.0 g |
| PEG4000 | 2.0 g | PEG4000 | 2.0 g | PEG4000 | 2.0 g |
| PEG400 | 1 g | Vitamin E | 1.0 g | PEG400 | 0.5 g |
| Total | 6 g | Total | 6 g | Vitamin E | 0.2 g |
| | | | | Total | 5.7 |

TABLE 6.5

The performance of each formulation

| Formulation | Parameter setting | Commentary |
|---|---|---|
| 4 | 70° C.; 180 rpm; 15 min | 3.1126 g yield. Film was very soft and oily. |
| 5 | 70° C.; 180 rpm; 15 min | 2.3095 g yield. Mixture was too soft to make a film. |
| 6 | 70° C.; 180 rpm; 15 min | 1.4419 g yield. Film was soft and not oily. However manufacturing difficulty was experienced. |

After the development of these prototype formulations, thermostable bacteria were incorporated into the film shown in FIG. 7. Bacteria viability was evaluated and it was found that viability was not maintained. It was hypothesized that by lowering the screw speed it could be able to protect the bacteria from mechanical damage due to the lower shear rate. In the following study, the screw speed was lowered to 40 rpm and 1.2±0.4 E5/mg (about 10% of loading dose) bacteria viability was obtained.

Example 7: Preparation of the HPC Micro-Needle Patches Containing a Micronized Vaccine Powder Using Anhydrous Solvent Casting Method For preparation of formulations for micro-needle patch formation, "formulation 4" of example 3 (0.8 g HPC, 0.2 g triacetin, 10 mL acetone), above, was chosen for testing and mixed with micronized PBV-preserved vaccine powders. The acetone was then partially evaporated to obtain a viscous (syrup) mixture containing 20% to 70% of acetone with the vaccine powders inside. The mixture was pressed inside an inverse micro-needle mold and remaining acetone was evaporated under vacuum at temperatures below 80° C. This resulted in a solid HPC micro-needle patch containing micronized PBV-preserved vaccine particle incorporated inside the patch for transdermal delivery. It should be noted that the temperature at which the patch can be formulated depends on the concentration and type of plasticizer used in the mixture. Any plasticizer that is dissolvable in acetone and not harmful to the dry vaccine powder could be used. It is also not absolutely necessary to use vacuum to remove the remaining acetone.

Example 8: Preparation of the HPC Micro-Needle Patches Containing a Micronized Vaccine Powder Using Heat Melted Mixtures This method is similar to the one described in the Example 7 with one important difference. No acetone or other solvent were used. The mixture of vaccine particles with PEO and plasticizer was transformed by heating into a liquid viscous state containing suspended vaccine particles. The mixture was then filled into a mold, and solidified into micro-needles upon cooling.

INDUSTRIAL APPLICABILITY

The invention applies to the manufacture of compositions used for delivery of sensitive biopharmaceuticals in regions where cold chain storage and/or clean water are not readily available.

In addition, the invention can be used for alternative delivery platforms, such as the manufacture of dissolvable films and micro-needle patches, which aid in the reduction of problems associated with needle-delivery.

REFERENCE SIGNS LIST dissolvable film (100)
first layer of polymeric composition (101)
second layer of polymeric composition (102)
carbohydrate-glass particle (110)
carbohydrate-glass matrix (111)
biopharmaceutical (112)
micro-needle patch (120)
first layer of patch (121)
second layer of patch (122)
micro needles (125)

What is claimed is:

1. A composition, comprising: an amorphous substrate including: a polymeric excipient and a plasticizer; and carbohydrate-encapsulated biopharmaceuticals embedded within said amorphous substrate; characterized in that: said polymeric excipient is soluble in both water and an organic solvent; and said carbohydrate-encapsulated biopharmaceuticals are not soluble in said organic solvent; wherein the carbohydrate-encapsulated biopharmaceuticals are encapsulated in carbohydrate-glass particles.

2. The composition of claim 1, wherein the polymeric excipient comprises:
hydroxypropyl cellulose and/or cellulose acetate.

3. The composition of claim 1, wherein the plasticizer comprises one or more from the group consisting of: polyethylene glycol, propylene glycol, triacetin, and poloxamer 407.

4. The composition of claim 1, wherein the carbohydrate-encapsulated biopharmaceuticals comprise one or more vaccine agents and/or probiotics.

5. The composition of claim 4, wherein said carbohydrate-glass particles comprise a particle size less than 50 microns.

6. The composition of claim 5, wherein said carbohydrate-glass particles comprise a particle size between 10 microns and 30 microns.

7. The composition of claim 1, wherein said carbohydrate glass particles consist essentially of: non-reducing sugars and/or derivatives thereof.

8. A composition, comprising: an amorphous substrate comprising between: 70 to 95 percent by weight hydroxypropyl cellulose and 5 to 30 percent by weight triacetin; and carbohydrate-encapsulated biopharmaceuticals embedded in said amorphous substrate, wherein the carbohydrate-encapsulated biopharmaceuticals are encapsulated in carbohydrate-glass particles.

9. The composition of claim 8, wherein said carbohydrate-encapsulated biopharmaceuticals comprise a vaccine agent and/or a probiotic.

10. The composition of claim 8, wherein said carbohydrate-glass particles comprise non-reducing sugars and/or derivatives thereof.

11. A medical delivery device for delivery of biopharmaceuticals to a patient, the medical delivery device comprising:
a vaccine agent and/or a probiotic encapsulated in carbohydrate-glass particles;
said carbohydrate-glass particles embedded in an amorphous polymer substrate;
wherein said amorphous polymer substrate is soluble in both water and an organic solvent; and wherein said carbohydrate-glass particles are not soluble in the organic solvent.

12. The medical delivery device of claim 11, wherein said amorphous polymer substrate comprises hydroxypropyl cellulose.

13. The medical delivery device of claim 12, said amorphous polymer substrate further comprises a plasticizer selected from the group consisting of: polyethylene glycol, propylene glycol, triacetin, and poloxamer 407.

14. The medical delivery device of claim 13, said device comprising a dissolvable film.

15. The medical delivery device of claim 13, said device comprising a patch.

16. The medical delivery device of claim 15, said device comprising a micro-needle patch.

* * * * *